United States Patent [19]

Kelley et al.

[11] Patent Number: 4,981,585
[45] Date of Patent: Jan. 1, 1991

[54] CENTRIFUGE SYSTEM AND FLUID CONTAINER THEREFOR

[75] Inventors: Thomas F. Kelley, Canton; Robert L. Scott, Medfield, both of Mass.

[73] Assignee: Norfolk Scientific, Inc., Norwood, Mass.

[21] Appl. No.: 372,874

[22] Filed: Jun. 28, 1989

Related U.S. Application Data

[62] Division of Ser. No. 797,873, Nov. 14, 1985, Pat. No. 4,846,974.

[51] Int. Cl.$^5$ ............................................. B01D 33/02
[52] U.S. Cl. ................................... 210/138; 210/144; 210/145; 210/360.1; 210/361; 210/363; 210/365; 210/782; 494/11; 494/12; 494/16; 494/45; 494/82; 494/84
[58] Field of Search .................. 210/360.1, 361, 363, 210/365, 782, 787, 789, 138, 143, 144, 145; 494/16, 17, 22, 37, 45, 84, 11, 12, 82

[56] References Cited

U.S. PATENT DOCUMENTS

| | | | |
|---|---|---|---|
| 3,779,451 | 12/1973 | Lehman | 494/84 |
| 4,255,256 | 3/1981 | Ferrante et al. | 210/789 |
| 4,464,167 | 8/1984 | Schoendorfer et al. | 494/37 |
| 4,530,691 | 7/1985 | Brown | 494/45 |
| 4,806,252 | 2/1989 | Brown et al. | 210/789 |
| 4,846,974 | 7/1989 | Kelley et al. | 210/380.1 |
| 4,855,042 | 8/1989 | Smith | 210/363 |

Primary Examiner—W. Gary Jones
Attorney, Agent, or Firm—Weingarten, Schurgin, Gagnebin & Hayes

[57] ABSTRACT

A disk shaped cassette for centrifugal fluid separation, particularly blood separation, and a drive system for high speed rotation of the cassette. The cassette is driven at speeds which permit very rapid separation of the blood in times on the order of seven (7) to twenty (20) seconds by an automated control. The cassette is supported by a flexible support coupling and mounting system that permits the entire rotating mass to spin about the center of mass unique to the particular cassette as filled. The cassette typically includes a peripheral collection chamber which may be either annular, lobed or channel shaped. A cassette enabled to hold plural separation tubes is also shown. A gel can be placed in the cassette with a density between the fluid components to be separated and after centrifuging maintains the component separation that centrifuging creates. Because the cassette disperses the fluid components, markings may be molded into the cassette or placed against it to permit volumetric gauging of the centrifuged components. The cassette is provided in various configurations to provide control over the exchange of fluid between collection chambers and to facilitate the separation functions.

27 Claims, 7 Drawing Sheets

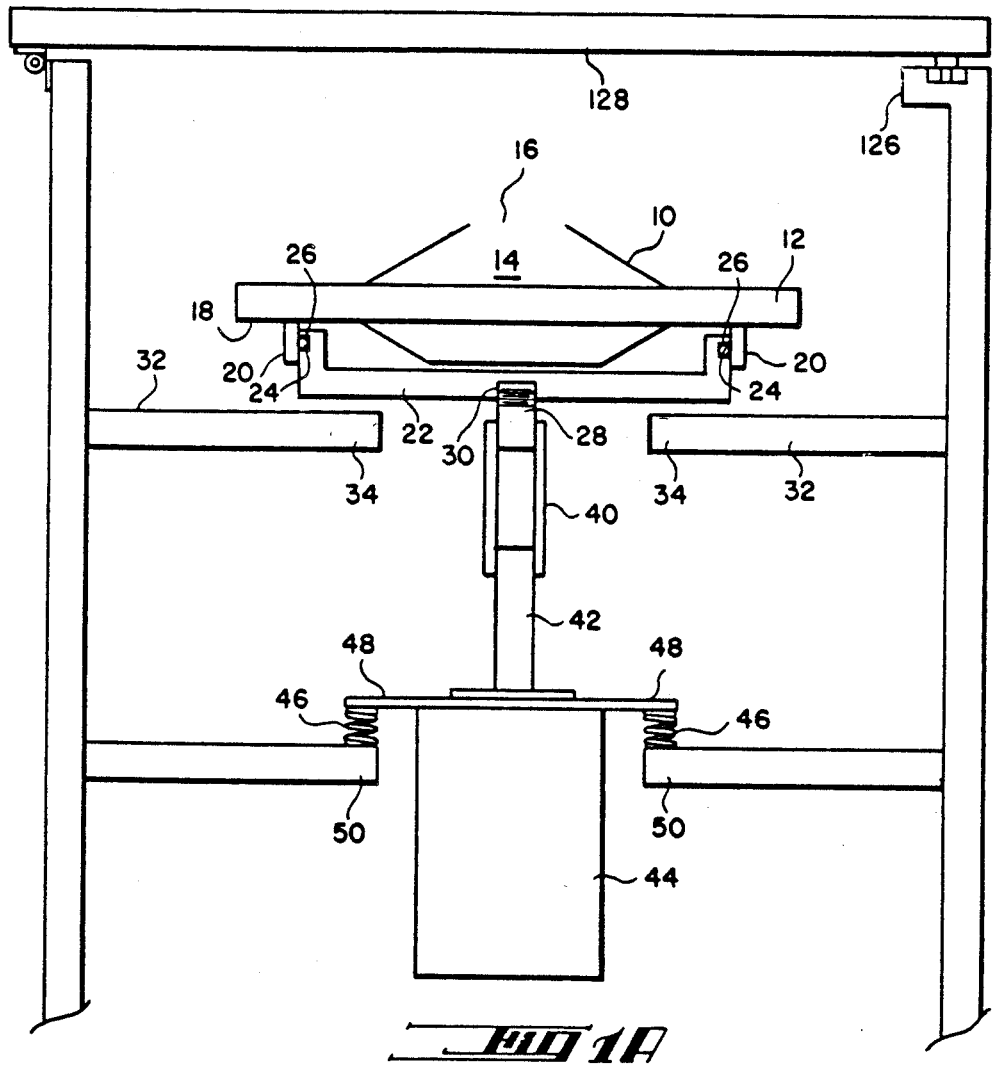
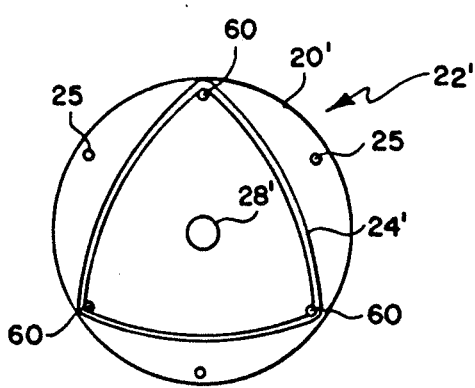
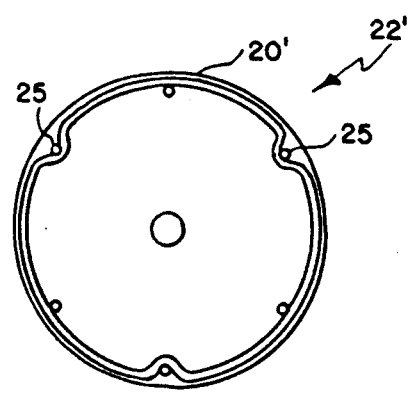

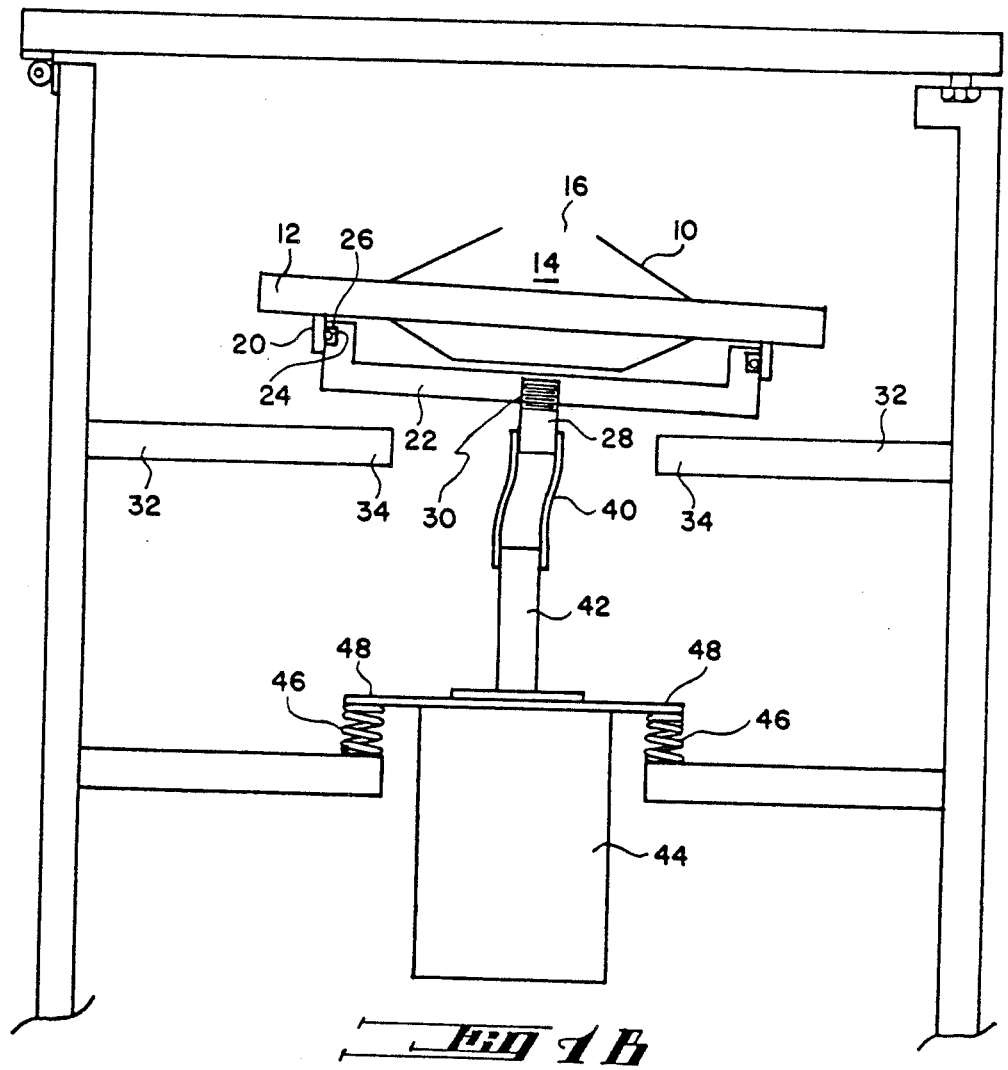
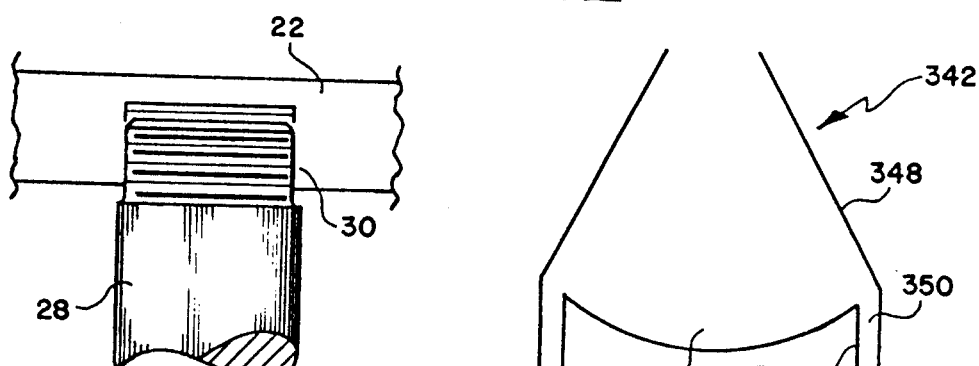

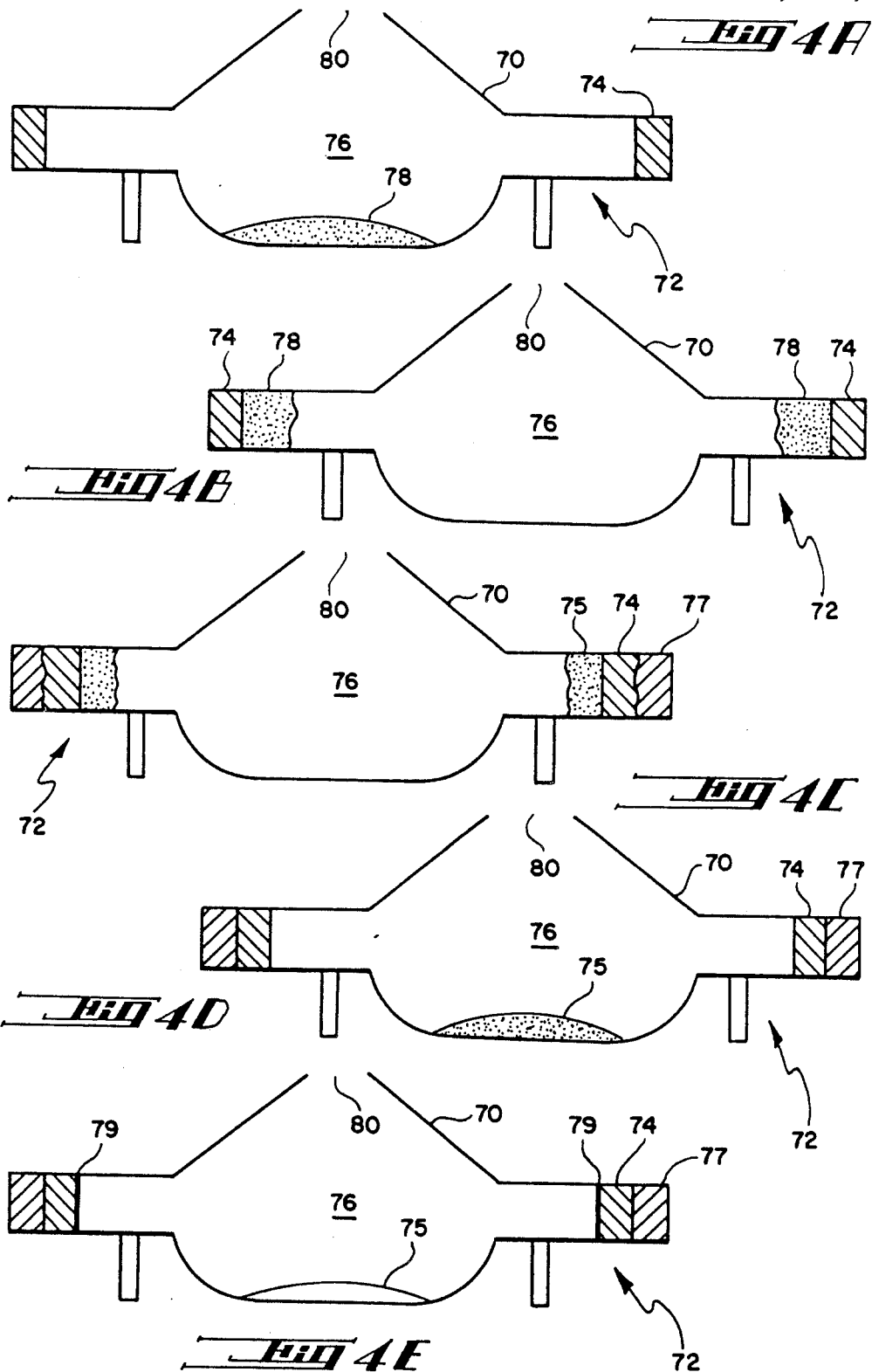

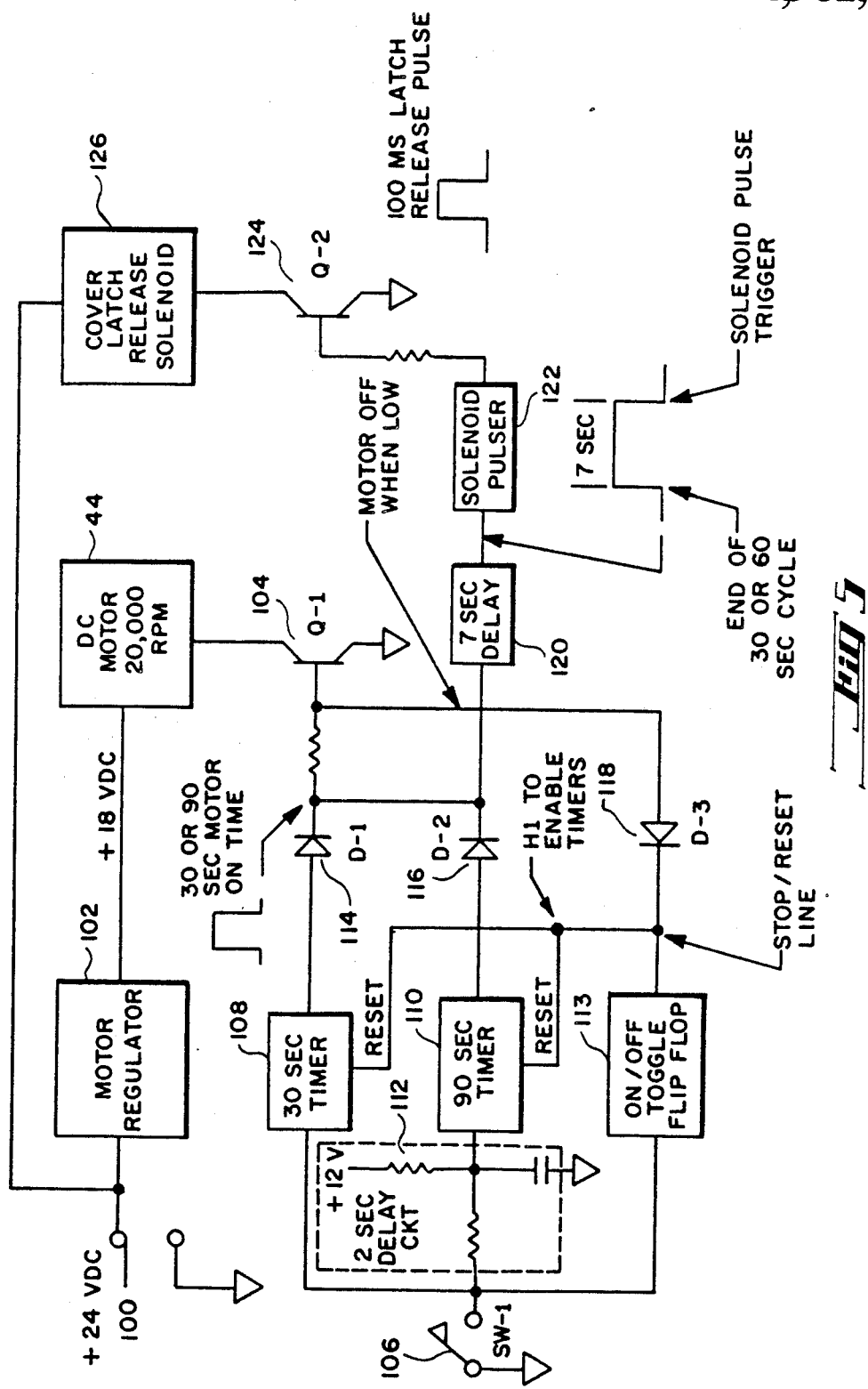

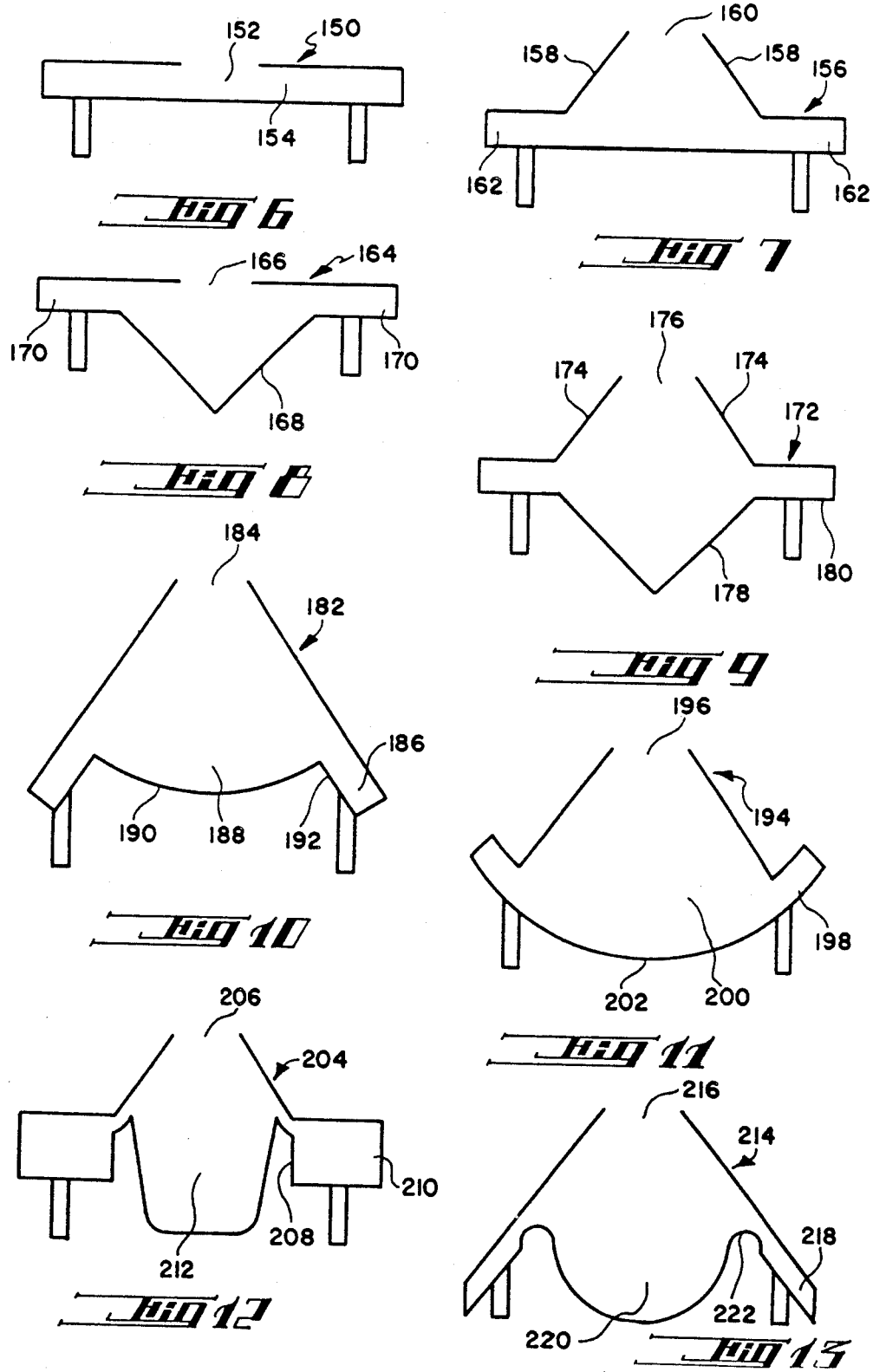

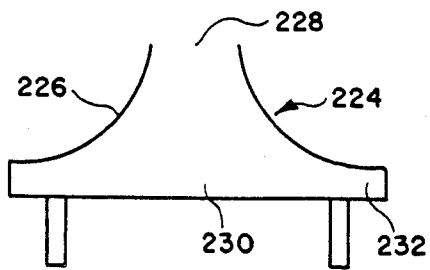
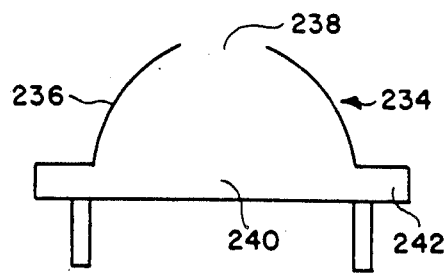
Fig. 14
Fig. 15
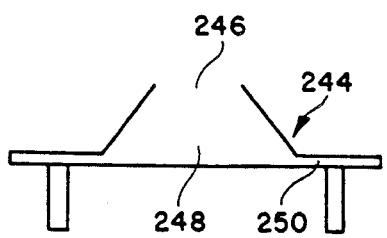
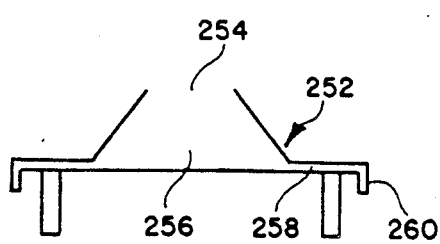
Fig. 16
Fig. 17
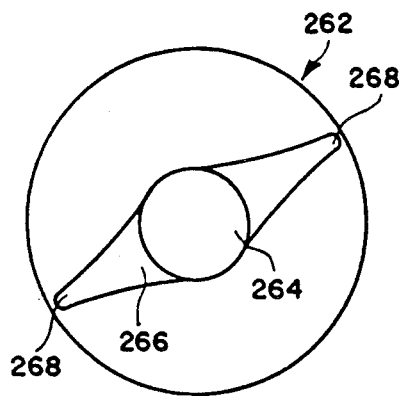
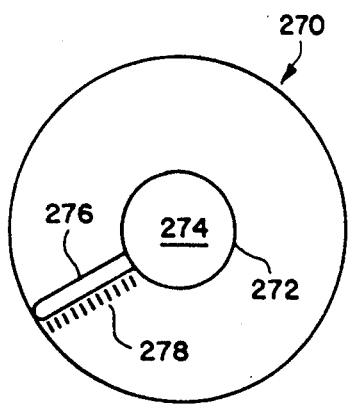
Fig. 18
Fig. 19

CENTRIFUGE SYSTEM AND FLUID CONTAINER THEREFOR

This application is a division of application Ser. No. 06/797,873, filed Nov. 14, 1985 now U.S. Pat. No. 4,846,974.

FIELD AND BACKGROUND OF THE INVENTION

The present invention relates to the field of fluid centrifuging and in particular to the centrifuging of blood specimens.

In the practice of medical analysis it is common to submit human blood samples to analysis for the concentrations of a large number of blood components useful in diagnosis and preventive medicine. To perform these analyses, it is common to separate whole blood into the components of plasma and particulates such as blood cells or to separate coagulated or clotted blood into serum and the solids as well by centrifuging. In centrifuging the serum or plasma is lighter in weight and collects radially closer to the spin axis of the centrifuged container. The container normally used has been a test tube, several of which are supported in a hub that is spun at speeds up to and slightly over three thousand revolutions per minute. Great care is needed to insure that the spinning hub is balanced, or the combined weight of test tube and contents, along with the hub can create a dangerous, uncontrolled vibration or worse.

Processing times for centrifuging blood by this technique typically run into as long as ten (10) or twenty (20) minutes. These times are unacceptable in many emergency conditions or to permit efficient analysis on a routine basis of a great many blood samples.

Typical approaches to blood centrifuging include use of a test tube that contains the blood sample which is in turn exposed to centrifuging in a rotary hub. The plasma or serum of the centrifuged sample is then removed by a withdrawing needle or other means. Care must be exercised to prevent the remixing of the centrifuged material before extracting of the component to be analyzed. A gel material may be added to help prevent this remixing.

The test tube system also suffers from the requirement that carefully measured amounts of the blood must be placed into the tube or tubes to be centrifuged in order to prevent the unbalanced rotation of the centrifuging hub. Such care adds to the time required to centrifuge blood and cuts down on the throughput of sample analysis.

More recently, cassette designs have been placed in use involving a rotating disk that has a circular valve separating radially separated compartments which opens under centrifuging forces to permit the heavier material to collect outwardly. Such cassette techniques also require many minutes, typically twenty (20), for the separation of blood. Initial mass unbalance conditions limit the centrifugal force that can be developed in such disks without causing vibration damage. Additionally, manufacturing tolerances are strict in order to maintain the rotational balance necessary for proper operation. This in turn makes such systems costly.

In addition, liquid clarification systems are in use using a high speed air bearing rotor. Such designs are not suitable for the centrifuging of such specimens as blood, and are extremely high cost.

BRIEF SUMMARY

These and other deficiencies of the prior art are overcome in a cassette and rotary drive according to the present invention. The rotary drive is coupled to a disk shaped blood cassette by a coupling mechanism that allows the disk to rotate about its real center of mass distinct from that of the drive or coupling mechanism. This allows very high rotation speeds, on the order of 20,000 RPM, at which blood separation can be accomplished in several seconds rather than the 10–20 minutes of the past. A gel may be used as a separation maintainer without adverse impact from any initial imbalance. The coupling mechanism automatically achieves self-balancing, insuring that rotation will be about the cassette's actual center of mass. A control system automatically runs the cassette up and down through the centrifuging speed on a prescribed schedule.

The cassettes are provided in different configurations to accomplish objectives ranging from simple and economical manufacture to configurations for the collecting chambers for the heavier and lighter components of the fluid that maintain separation or promote drainage, provide a scale for measuring separate fraction volumes, and to permit concentration and collection of very small relative volumes as is useful in urine analysis.

DESCRIPTION OF THE DRAWING

These and other features of the present invention are more fully described in the following solely exemplary detailed description and accompanying drawing of which:

FIGS. 1A–1B are illustrations of a high speed rotary drive and fluid cassette at rest and in rotation according to the invention;

FIG. 2A–2B show an alternative O-ring coupling scheme between cassette and rotary drive;

FIG. 3 illustrates a shaft coupling arrangement to permit extension with rotation of the cassette according to the invention;

FIGS. 4A–4E illustrate the steps in the process of utilization of a cassette according to the present invention for separation of blood components;

FIG. 5 is a schematic diagram of a control system providing automated run up and run down of a cassette utilizing a rotary drive according to the present invention;

FIGS. 6–25 illustrate different preferred forms for the cassette of the present invention;

DETAILED DESCRIPTION

Figure 20:
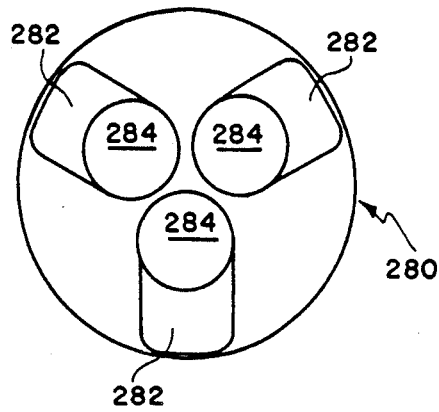

The present invention contemplates a cassette and rotational drive for providing centrifugal separation of fluid components, particularly for use in blood analysis, which permits high speed rotation for fast centrifugal separation in combination with cassette configurations which promote various functions.

A system according to the invention is illustrated in FIGS. 1A–1B wherein is shown a cassette 10 of generally disk shape having a peripheral annular collection chamber 12 and a central collection chamber 14 with an aperture 16 leading into the chamber 14 from the top. The cassette 10 has an underbody 18 from which a collar 20 extends downwardly. A cassette holder 22 contains an O-ring 24 within a groove 26 which mates with the collar 20 to provide a mechanism for removably holding the cassette 10 to the coupling 22.

The holder 22 is supported on a shaft 28 by a loosely held screw thread arrangement 30 illustrated more fully in FIG. 3. The arrangement permits the coupling 22 to lie substantially adjacent to an inner support plate 32 of a cabinet for the system when at rest, being supported in regions 34 to allow press installation of cassette 10 upon the holder 22. Upon rotation of the shaft 28, the screw arrangement 30 causes the holder 22 to elevate, permitting it to assume a balanced rotational configuration, which may not necessarily be coaxial or in the horizontal plane, as illustrated in FIG. 1B.

This capability is facilitated by a flexible support coupling 40 between shaft 28 and a shaft 42 of a drive motor 44. The coupling 40 may typically be an elastomeric sleeve joining the two shaft portions 28 and 42. Other types of flexible couplings, that provide some angular and offset resiliency between the shafts may be utilized, such as helical wire wound shafts, spring loaded universal joints, and the like.

The motor 44 is further supported through a resilient mount 46 between a lip 48 extending outwardly from the motor chassis in the vicinity of the shaft 42 and an apertured plate 50. The resilient mount 46 may be a rubber, foam rubber or other element which permits the motor 44 to assume an other than strictly vertical orientation and which cooperates with the support coupling to the cassette to permit the cassette to rotate about its actual center of mass.

The system of motor drive and cassette illustrated above with respect to FIGS. 1A and 1B permits high speed rotation of the cassette 10 by permitting the entire rotating mass to rotate about a center of balance which may be slightly displaced from the center of the motor shaft 42. Upon acceleration by the motor 44, the combination of coupling 22 and cassette 10, in accelerating to high revolutions in the neighborhood of 20,000 RPM, will self-balance themselves to a substantially vibrationless high speed rotation condition through the cooperation of the flexible shaft 40, and flexible mount 46. This allows the extremely high speed centrifuging of blood samples, allowing a fully acceptable centrifuge separation typically in seven (7) to twenty (20) seconds. The ability of the system to self-balance further permits the utilization of cassettes 10 manufactured in economical, for example molding, processes not subject to meticulous and costly balancing of the cassette body itself. In addition, the placement of samples, including separation maintenance gels, within the cassette 10, particularly if the gel flows during storage prior to use, can result in significant unbalance of the cassette 10 at the time when it is placed upon the holder 22 for acceleration. Such unbalances can be accommodated by the drive system of the present invention, permitting the high-speed short-term centrifuging of which the invention is capable.

FIGS. 2A and 2B illustrate an alternative holder 22' having an O-ring 24' wrapped around a set of support pins 60 and adapted for a rotation about a shaft 28' from the drive system. A collar 20' from the cassette, not shown, is press fit outside of O-ring 24'. Upon acceleration, as illustrated in FIG. 2B, the O-ring 24' is centrifugally urged outward conforming to the cassette collar 20' and providing an additional frictional coupling between support and cassette. Pins 25 prevent loss of the O-ring if the holder 22' is accelerated without a cassette.

The steps in the process of separation of components of an anticoagulated whole blood sample according to one embodiment of the present invention are illustrated with respect to a cassette 70 in FIGS. 4A–4E. The details of the rotational drive are omitted to promote clarity of illustration. The cassette 70 has a peripheral annular collection chamber 72, which contains an annular band of gel 74, and a central collection chamber 76 to which a whole blood sample 78, typically 3 cc, is inserted through an aperture 80. The gel 74 is typically a viscous material which has a density intermediate that of blood plasma and the remaining blood components. Gels are selected, aside from density, for their insolubility in blood components and for purity, inertness and time and temperature stability.

Immediately upon acceleration of the cassette 70, and as illustrated in FIG. 4B, the whole blood 78 will be peripherally forced against the gel 74.

During the seven (7) to twenty (20) seconds of high speed rotation, the cellular components will displace the gel 74 of lower density and collect as packed cells 77 in the peripheral collection chamber 72 as shown in FIG. 4C. Platelets within the plasma 75 will migrate through the gel 74 at a slower rate, depending upon the length of centrifuging and the density of the gel. The remaining plasma 75 will be rich or partially depleted in platelets. By continuing the process of high speed rotation for from thirty (30) to ninety (90) seconds, the remaining plasma 75 will be generally free of platelets. FIG. 4D illustrates the separated blood in the cassette 70 after rotation is stopped. The central chamber 76 will contain the plasma while the gel 74 will act as a separation maintaining barrier holding the packed cells in the peripheral annular chamber 72. The positional stability of the gel 74 will insure that the separation is maintained for long periods of time and the plasma will retain its separated properties. If the gel is of suitable properties, a layer 79 of platelets will deposit on the inner wall of gel 74 as shown in FIG. 4E. These can be separately collected.

The steps in the process of separation of components of untreated (not anticoagulated) whole blood are also illustrated in FIGS. 4A–4E. Such blood, if allowed to stand in cassette 70, will eventually clot. If then centrifuged, the clot or coagulum collects in peripheral chamber 72 behind the gel 74, if present. If the (untreated) blood sample is processed before clotting occurs or is complete, the collected serum can remain fluid for sufficient time for some analyses. That serum will eventually clot due to the presence of polymeryable protein. Cassettes containing such a serum clot can be reprocessed, forcing the serum clot against the gel, while the serum trapped in the clot is left in an inner band. Upon stopping, this serum can be extracted and thus made available for analysis.

The steps of FIGS. 4A–4E are typically achieved by an automated control system for the motor 44 as illustrated in FIG. 5. As shown in FIG. 5, the motor 44 is activated from a supply source 100 through a regulator 102 which maintains a regulated voltage for the motor 44. A transistor switch 104 is activated by the timing circuitry to direct the current through the motor 44 to ground, permitting on-off control of the motor 44. A switch 106 is operator activated and controls a short interval timer (seven (7) to twenty (20) seconds typically) 108, a long interval (typically ninety (90) seconds) timer 110 through a delay circuit 112, constituting a low-pass filter, and further controls an on-off toggle flip-flop 113. The timers 108 and 110 provide output pulses of respective short and long durations through diodes 114 and 116 to activate the base of the transistor switch 104. The toggle 113 acts through a reverse diode 118 to bias off the transistor 104 permitting instantaneous operator cessation of rotation through a second activation of the switch 106.

In operation, the closure of the switch 106 for a short interval will activate the timer 108, and toggle the flip-flop 113 into an "on" state, energizing the transistor 104 for the short interval of the timer 108. The operator may activate the long interval timer by holding the switch 106 closed a sufficient length of time to overcome the delay of the delay circuit 112, thereby activating the timer 110 to control the "on" time of the transistor 104. As indicated above, a second push of the switch 106 will toggle the flip-flop 113 to its opposite state, permitting instant deactivation of the motor 44 by turning off the transistor switch 104.

When either timer 108 or 110 times out, a seven (7) second delay circuit 120 is activated which in turn activates a solenoid drive circuit 122 which activates a transistor switch 124. The transistor switch 124 activates a latch release 126 which cooperates with a cover 128 over the area of cassette 10. This additional feature provides safety interlocking by closing off the region of the centrifuge action from the environment. The cover 128 is typically supported above the plate 32. The toggling of the flip-flop 113 to the "off" state also resets the timers 108 and 110.

FIGS. 6–25 show different geometric configurations for the cassette in which the blood is centrifuged. Gels may be used in any of them. FIG. 6 shows a basic planar cassette 150 with opening 152 in which the blood is introduced. FIG. 7 shows cassette 156 which possesses a cone-shaped top 158, the cone-shaped top having an opening 160 and an annular region 162. The cone-shaped top 158 allows the cassette to be more easily filled with a sample. FIG. 8 shows a cassette 164 with an opening 166 and a conical bottom 168 as well as an annular region 170. The conical bottom 168 permits the plasma to be more easily recovered after centrifugation. FIG. 9 shows a cassette 172 which combines the features of the cassettes in FIGS. 7 and 8. Cassette 172 includes a cone-shaped top 174 with an opening 176, A conical bottom 178, and an annular region 180. Cassette 172, therefore, is easy to fill because of cone-shaped top 174 and plasma recovery is made easier because of conical bottom 178. Cassette 182 in FIG. 10 possesses an opening 184, an annular region 186 and a central chamber 188 with a rounded or conical bottom 190. Annular region 186 is biased downwardly such that a physical barrier 192 exists and so that gravity can be utilized to maintain the separation between those materials in annular region 186 and central chamber 188 while permitting free flow to the periphery while centrifuging. The cassette 194 shown in FIG. 11 has an opening 196, an annular region 198 and a central chamber 200 with a conical or rounded bottom 202. The annular region 198 is biased upwardly to provide for better drainage to central chamber 200, for the product which has been centrifuged to the annular region. A gel will typically be used here. The cassette 204 in FIG. 12 has an opening 206 and a physical barrier 208 to separate annular region 210 and central chamber 212. The use of barrier 208 assists in the isolation of the product in annular region 210 and central chamber 212. FIG. 13 shows cassette 214 with a central opening 216, an annular region 218 and a central chamber 220. A physical barrier 222 is also shown to separate annular region 218 from central chamber 220. Annular region 218 is also biased downwardly so that it has the further advantage of gravity retaining the product which has been centrifuged into the annular region, as was present in cassette 182 in FIG. 10. FIG. 14 shows cassette 224 with an upwardly sloping concave top 226; top 226 having an opening 228 for the introduction of a sample into the interior of the cassette. The cassette 224 has a central chamber 230 and annular region 232. The upwardly sloping concave top 226 enchances the pourability of material from within the cassette 224. Cassette 234 shown in FIG. 15 possesses a rounded convex top 236 with an opening 238 as well as central chamber 240 and annular region 242. The rounded top 236 retards the spilling of material from within cassette 234.

The cassettes shown in FIGS. 16 and 17 may be used in the measurement of the percent of packed red cells by volume (known as a hemotocrit) which make up a given sample of whole blood. Cassette 244 in FIG. 16 possesses an opening 246 to introduce a sample into central region 248. A thin or tapered annular region 250 is also present and allows blood samples to be spun such that the packed red cells are spread out along the plane of the annular region 250 together with the plasma or liquid portion of the blood sample. As a result of the solid and liquid portions of the blood sample being maintained in annular region 250, the cassette can be used to measure the volume of packed red cells versus the volume of total sample present, using methods and devices known in the art, to get a hematocrit reading for the centrifuged blood sample. Cassette 252 in FIG. 17 possesses an opening 254 to introduce the sample into central chamber 256 and a thin or tapered annular region 258 which operates in a similar manner to element 250 in cassette 244 of FIG. 16. Cassette 252 also possesses a terminal well region 260 which is in contact with annular region 258. Cassette 252 is also used to measure hematocrit. The presence of well region 260 enhances the resolution of such a measurement by expanding the region of cells over which the measurement is taken. By virtue of an expansion of this nature, white blood cells can be detected. Blood is added until the white cells occupy a very thin region 258. The region 258 is made typically 0.1 mm.

Figure 21:
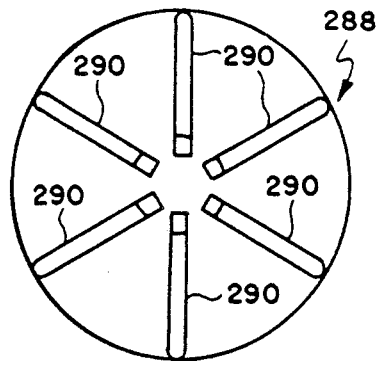
Figure 22:
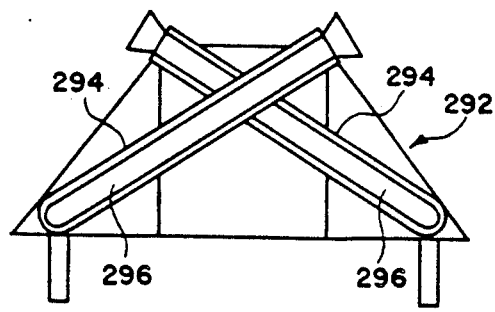
Figure 23:
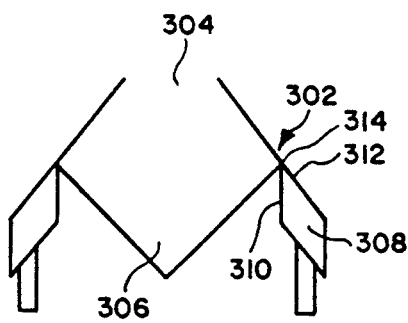
Figure 24:
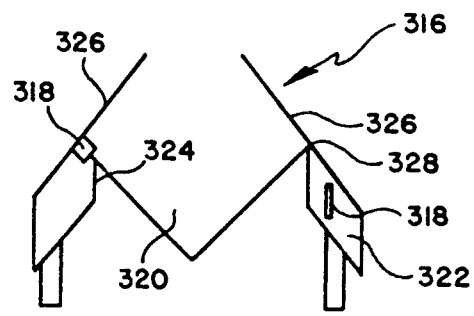

FIGS. 18–20 show further cassettes with single or multiple radial or lobed peripheral chambers of various shapes and arrangements. Cassette 262 in FIG. 18 possesses a central opening 264, a central chamber 266 and progressively narrowing lobed peripheral chambers 268. The narrowing of the lobed peripheral chambers 268 aids in the recovery of solid material suspended with the centrifuged liquid sample where the solid material is present in very small amounts, for example, recovery of particulate matter from a urine sample. Cassette 270 is FIG. 19 shows a central opening 272 and a central chamber 274 located below the central opening. A radially extending peripheral chamber 276 is in communication with central chamber 274. Radial peripheral chamber 276 can be calibrated for volume measurement with the calibration index 278 located adjacent to lobed peripheral chamber 276. In FIG. 20, a cassette 280 has plural, separate radial chambers 282 and separate access openings 284 to permit processing of multiple samples in a single cassette. In FIG. 21, there is shown a cassette 288 which is adapted to hold plural small tubes 290, each providing individual sample centrifuging. FIG. 22 shows a cassette 292 having cavities 294 adapted to hold small tubes 296 at a slant for separate centrifuging. FIGS. 23–24 show cassettes wherein the annular region of each cassette is mechanically sealed off from the central chamber before or after centrifugation. However, during the centrifuging process, the mechanical seal is opened due to hydrostatic pressure. FIG. 23 shows cassette 302 having opening 304, central chamber 306 and annular region 308. The annular region 308 is biased downwardly so as to take advantage of gravitational forces. Physical barrier 310 is in physical contact with top wall 312 at position 314. During the centrifugation process, physical barrier 310 and top wall 312 separate to provide an opening at position 314 for communication between central chamber 306 and annular region 308. The volume ratio between chambers 308 and 306 is on the order of 1 to 2. FIG. 24 shows cassette 316 which is similar to cassette 302 in FIG. 23, with the addition of elements 318 which provide for fluid communication between central chamber 320 and annular region 322 and are positioned between physical barrier 324 and top wall 326 prior to centrifugation as shown on the left side of the drawing. During centrifugation the hydrostatic pressure deforms cassette 316 allowing element 318 to enter into the annular region 322. Once the centrifuging process is finished, physical barrier 324 and top wall 326 come together in physical contact at position 328 and element 318 remains in annular region 322. FIG. 25 shows another embodiment of this type of isolated cassette wherein cassette 342 has a physical barrier 346 and top wall 348, thereby separating annular region 350 from central chamber 351.

Figure 26A:
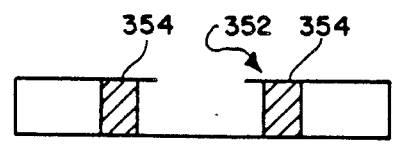
FIGS. 26A–26B illustrate height and width considerations for gels used in the invention.
Figure 26B:
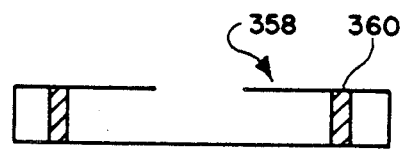

The cassettes shown in FIGS. 6–25 may be used either with or without a separation gel, previously described. These gels are placed within the cassettes so as to provide a barrier between the central chamber of each cassette and the cassette's annular or lobed region. The volume of gel necessary in the cassette in order to provide for proper separation of sample components will vary depending upon the volume of space between the gel and the outer wall of the cassette itself. In order to provide for proper separation, this ratio of gel 354 radial length to height should be greater than approximately 0.6, as shown in cassette 352 in FIG. 26A. In comparison, cassette 358 in FIG. 26B shows gel 360 of too low an aspect ratio. Cassette 358 would not provide a proper separation because the gel volume is not stable. Platelets collected on an inner surface of gel can be washed into the serum or plasma and that fluid separately centrifuged to get a platelet packed volume.

It is possible to include with the cassette a means for self filling such as by providing evacuated cassettes, as is practiced with test tubes, or a mechanical withdrawal means.

Modifications may be made to the above-described system without departure from the scope of the invention which is solely defined in the following claims:

What is claimed is:

1. A high speed rotary drive for a centrifugal separation cassette comprising:
    first and second spaced apart shafts each adapted for rotation and each having first and second ends;
    means for coupling a centrifugal separation cassette to the first end of said first shaft to support said cassette thereon and to transmit rotary torque thereto;
    means for driving said first end of said second shaft about an axis at high rotary speeds;
    means coupled between said second end of said second shaft and said second end of said first shaft for supporting said first shaft off of said spaced apart second shaft and for flexibly coupling said first shaft to said second shaft to both transmit rotation from said second shaft to said first shaft and to permit said first shaft to rotate about an axis that is offset from the axis of the second shaft.

2. The rotary drive of claim 1 wherein said coupling means includes means for removably coupling to said cassette.

3. The rotary drive of claim 2 further including means associated with said coupling means for engaging a collar associated with an underside of said cassette to provide the removable coupling.

4. The rotary drive of claim 1 further comprising:
    a centrifugal separation cassette; and
    wherein said coupling means includes an O-ring between said cassette and coupling means.

5. The rotary drive of claim 4 further including means for accommodating radial expansion of the O-ring under centrifugal force of rotation of said cassette and coupling means.

6. The rotary drive of claim 4 wherein the cassette includes means receiving plural tubes for fluid containment.

7. The rotary drive of claim 1 further including means for flexibly supporting said driving means to permit the axis of said driving means to take different positions upon activation.

8. The rotary drive of claim 7 wherein said flexibly supporting means includes a member positioned about said second shaft in such a way that said driving means are generally on one side thereof and said first shaft is generally on the other side thereof.

9. The rotary drive of claim 7 wherein said supporting means includes a flexible mount.

10. The rotary drive of claim 1 wherein said driving means includes means for rotating said shaft at rotational rates above five thousand revolutions per minute.

11. The rotary drive of claim 10 wherein the rotary rate is approximately twenty thousand revolutions per minute.

12. The rotary drive of claim 1 further including means for automatically controlling said driving means to accelerate to and decelerate from the high rotary speed within a predetermined time.

13. The rotary drive of claim 12 further including means providing operator selection of a plurality of said predetermined times.

14. The rotary drive of claim 1 wherein said coupling means includes means for allowing elevation of said cassette away from said first shaft upon activation of said driving means.

15. The rotary drive of claim 14 wherein said elevating means includes a mating screw thread joint between the first shaft and the coupling means.

16. The rotary drive of claim 14 further including means for supporting said coupling means independently of said first shaft when said driving means is not activated.

17. The rotary drive of claim 14 further including means for flexibly supporting said driving means to permit the axis of said driving means to take different positions upon activation.

18. The rotary drive of claim 1 wherein said supporting means includes a flexible shaft coupled between said first and second shafts.

19. The rotary drive of claim 1 wherein said supporting and flexibly coupling means includes a flexible sleeve disposed about said first shaft and said second shaft.

20. The rotary drive of claim 1 wherein said supporting and flexibly coupling means includes a helical wire wound shaft.

21. The rotary drive of claim 1 wherein said supporting and flexibly coupling means includes a spring loaded universal joint.

22. A centrifuge comprising:
- a first shaft and a spaced apart second shaft, each adapted for rotation and each having first and second ends;
- a motor for rotating said first end of said second shaft about an axis at high speeds;
- a centrifugal separation member;
- means for coupling said first end of said first shaft to said centrifugal separation member to transmit rotary torque thereto;
- means coupled between said second end of said first shaft and said second end of said second shaft for supporting said first shaft off of said spaced second shaft and for flexibly coupling said first shaft to said second shaft to transmit rotation from said second shaft to said first shaft and to permit said first shaft to rotate about an axis that is offset from the axis of the second shaft in response to unbalance in the centrifugal separation member.

23. The centrifuge of claim 22 wherein said coupling means includes means for allowing elevation of said centrifugal separation member away from said first shaft upon activation of said driving means.

24. The centrifuge of claim 22 further including means for flexibly supporting said driving means to permit the axis of said driving means to take different positions upon activation.

25. The centrifuge of claim 22 wherein said supporting and flexibly coupling means includes a flexible sleeve disposed about said first shaft and said second shaft.

26. The centrifuge of claim 22 wherein said supporting and flexibly coupling means includes a helical wire wound shaft.

27. The centrifuge of claim 22 wherein said supporting and flexibly coupling means includes a spring loaded universal joint.

* * * * *

UNITED STATES PATENT AND TRADEMARK OFFICE
CERTIFICATE OF CORRECTION

PATENT NO. : 4,981,585
DATED : January 1, 1991
INVENTOR(S) : Thomas F. Kelley, et al.

It is certified that error appears in the above-identified patent and that said Letters Patent is hereby corrected as shown below:

Column 5, line 45, "opening 176. A" should read --opening 176. a--.

Column 6, line 20, "hemotocrit" should read --hematocrit--.

Signed and Sealed this

Twenty-ninth Day of September, 1992

Attest:

DOUGLAS B. COMER

*Attesting Officer*     *Acting Commissioner of Patents and Trademarks*